United States Patent
Schmidt et al.

(10) Patent No.: US 7,200,528 B2
(45) Date of Patent: Apr. 3, 2007

(54) METHOD FOR EVALUATING A SEQUENCE OF DISCRETE READINGS

(76) Inventors: Georg Schmidt, Belgradstrasse 19, 80796, Munich (DE); Axel Bauer, Georg-Habel-Strasse 12, 81241, Munich (DE)

(*) Notice: Subject to any disclaimer, the term of this patent is extended or adjusted under 35 U.S.C. 154(b) by 0 days.

(21) Appl. No.: 10/535,921

(22) PCT Filed: Nov. 27, 2002

(86) PCT No.: PCT/DE02/04349

§ 371 (c)(1),
(2), (4) Date: May 23, 2005

(87) PCT Pub. No.: WO2004/049190

PCT Pub. Date: Jun. 10, 2004

(65) Prior Publication Data

US 2006/0064285 A1    Mar. 23, 2006

(51) Int. Cl.
*G06F 15/00* (2006.01)
*A61B 5/02* (2006.01)

(52) U.S. Cl. ...................... 702/189; 600/481
(58) Field of Classification Search ............ 702/189, 702/33, 35, 56, 127, 190, 196–199; 600/481, 600/483, 508, 516, 519
See application file for complete search history.

(56) References Cited

U.S. PATENT DOCUMENTS 6,016,462 A * 1/2000 Schneider et al. ............ 702/14

* cited by examiner

*Primary Examiner*—Manuel L. Barbee
(74) *Attorney, Agent, or Firm*—Milde & Hoffberg, LLP

(57) ABSTRACT

The invention relates to a method for evaluating a sequence of discrete measured values whereby an attribute is assigned to each measured value before evaluation that includes the same properties for all measured values, and whereby a criterion is established for the attribute and the length of a chain from the sequence of discrete measured values.

16 Claims, 7 Drawing Sheets

Figure 1

Schematic representation of the evaluation of a sequence of measured values based on the invention a. Sequence of measured values M to be analyzed:

|       | M1 | M2 | M3 | M4 | M5 | M6 | M7 | M8 | M9 | M10 | M11 | M12 | M13 |
|-------|----|----|----|----|----|----|----|----|----|-----|-----|-----|-----|
| value | 13 | 16 | 17 | 14 | 19 | 17 | 13 | 9  | 5  | 21  | 17  | 14  | 13  | b. Assignment of attribute A to each of the measured values, e.g., assignment of the differential between the previous measured value: $A = M(x) - M(x-1)$.

|        | M1 | M2 | M3 | M4 | M5 | M6 | M7 | M8 | M9 | M10 | M11 | M12 | M13 |
|--------|----|----|----|----|----|----|----|----|----|-----|-----|-----|-----|
| value  | 13 | 16 | 17 | 14 | 19 | 17 | 13 | 9  | 5  | 21  | 17  | 14  | 13  |
| attrib |    | 3  | 1  | -3 | 5  | -2 | -4 | -4 | -4 | +16 | -4  | -3  | -1  | c. Definition of a criterion to select the measured values, e.g. K = 1 if A > 0. If the criterion is fulfilled for the attribute of a measured value, then the measured value becomes the event E.

|           | M1 | M2 | M3 | M4 | M5 | M6 | M7 | M8 | M9 | M10 | M11 | M12 | M13 |
|-----------|----|----|----|----|----|----|----|----|----|-----|-----|-----|-----|
| value     | 13 | 16 | 17 | 14 | 19 | 17 | 13 | 9  | 5  | 21  | 17  | 14  | 13  |
| attribute |    | 3  | 1  | -3 | 5  | -2 | -4 | -4 | -4 | +16 | -4  | -3  | -1  |
| criterion |    | 1  | 1  | 0  | 1  | 0  | 0  | 0  | 0  | 1   | 0   | 0   | 0   |
| event     |    | E1 | E2 |    | E3 |    |    |    |    | E4  |     |     |     | d. Creation of a table in which chains K of measured values are entered about the selected events E (some fields are empty because of the short output signal).

|    |    |    |    |    |    | E  |    |    |    |    |    |    |
|----|----|----|----|----|----|----|----|----|----|----|----|----|
| K1 |    |    |    |    |    | 13 | 16 | 17 | 14 | 19 | 17 | 13 | 9  |
| K2 |    |    |    |    |    | 13 | 16 | 17 | 14 | 19 | 17 | 13 | 9  | 5  |
| K3 |    |    |    | 13 | 16 | 17 | 14 | 19 | 17 | 13 | 9  | 5  | 21 | 17 |
| K4 | 14 | 19 | 17 | 13 | 9  | 5  | 21 | 17 | 14 | 13 |    |    |    | e. Formation of the Schmidt-Bauer Transformation (SBT) by averaging the chains.

|     |    |    |    |    |    | E     |       |       |      |       |       |       |       |
|-----|----|----|----|------|------|-------|-------|-------|------|-------|-------|-------|-------|
| K1  |    |    |    |      |      | 13    | 16    | 17    | 14   | 19    | 17    | 13    | 9     |
| K2  |    |    |    |      | 13   | 16    | 17    | 14    | 19   | 17    | 13    | 9     | 5     |
| K3  |    |    | 13 | 16   | 17   | 14    | 19    | 17    | 13   | 9     | 5     | 21    | 17    |
| K4  | 14 | 19 | 17 | 13   | 9    | 5     | 21    | 17    | 14   | 13    |       |       |       |
| SBT | 14 | 19 | 15 | 14.5 | 13   | 12    | 18.25 | 16.25 | 15   | 14.5  | 11.67 | 14.33 | 10.33 |

METHOD FOR EVALUATING A SEQUENCE OF DISCRETE READINGS

BACKGROUND OF THE INVENTION

The invention relates to a method for evaluating a sequence of discrete measured values whereby an attribute is assigned to each measured value before evaluation that includes the same properties for all measured values, and whereby a criterion is established for the attribute and the length of a chain from the sequence of discrete measured values.

The investigation of sequences of discrete measured values occurs in many realms of technology. Thus, for example, oscillation samples for function checks of machinery with rotating or reciprocating machine parts are evaluated using Fourier analysis in order to determine the frequencies obtained in each oscillation sample. Otherwise unrecognizable function breakdowns may be identified from the determined frequencies, such as incipient damage to bearings etc.

SUMMARY OF THE INVENTION

The object of the invention is to provide a method to evaluate a sequence of discrete measured values such as, for example, measured values based on oscillation samples, repetitive processes, or processes whose time parameter alters, that may be determined with the parameters that define the characteristic properties of the measured values even if concealed.

This object is achieved according to the invention the following method:.

An attribute is attached to each measured value whereby this attribute possesses the same characteristic for all measured values.

Those measured values thus possessing attributes are selected whose attribute fulfills a specific common criterion, and each is designated as a specific measured value or event.

A chain of a specific length is selected from the sequence of discrete measured values.

From this selected chain, partial chains are formed, each of which is centered about a selected event, whereby the other measured values of the partial chains in the original sequence are positioned to both sides of the central event.

The measured values of individual partial chains are arranged according to their position in that particular partial chain, such that the measured values of the central event that are located at the same position around that central event are positioned together.

All grouped measured values for the same positions within the selected partial chains are determined, and the sequence of the measured values thus determined is designated in the sequence dictated by the chain of measured values.

Based on the invention, in a first step, all measured values of the signal are provided with a specific attribute that characterizes the measured values in a certain property. In principle, any type of attribute is conceivable. In a simplified case, for example, the attribute may consist of the differential from the previous attribute. The attribute, however, need not be derivable from the signal to be analyzed. It is also possible to provide the measured values of the signal to be analyzed with an attribute from a second synchronous signal such as, for example, the measured values of an EKG signal with attributes from a blood-pressure signal designated at the same time.

From the measured values thus assigned attributes, at least some measured values are selected whose attribute fulfills a specific criterion. If, for example, all measured values are assigned the attribute of the differential from the previous measured value, then the selection criterion might be that the attribute is negative, i.e., the measured value is greater than the previous one. The selected measured values should be named within the following "events." A chain of measured values is then assigned to each event whose central element is the event itself, surrounded by the measured values that are positioned within the output signal before or after the event. The chains formed in this manner, whose lengths may be freely defined, are positioned in a table "under one another", whereby each row of the table corresponds to a chain of measured values. It is significant that the measured values occupy the same position under one another with respect to the event. If the criterion applies to a relatively large portion of the measured values, then measured values of the output signals are represented in the table several times dependent on the selected chain length, i.e., the table contains redundant information based on the methodology. In a subsequent step, the median values of a particular column are formed, i.e., the measured values of the same position with respect to selected measured values are determined.

In this manner, an output signal of any length may be transformed into a relatively short sequence, referred to hereafter as the "Schmidt-Bauer Transformation" (SBT). The SBT characterizes the output signal of any length dependent on the selected attribute and the selected criterion, which results in data reduction. The SBT may be evaluated in different ways such as, for example, in the time or frequency domain.

It has been shown that the evaluation method according to the invention allows determination of a large number of parameters that might not be apparent from the sequence of measured values alone.

Thus, for example, the base frequencies combining to produce an oscillation sample of a machine with rotating or reciprocating parts may be determined using analysis similar to Fourier analysis, whereby frequencies become apparent that are, for example, "harmful frequencies" that indicate damage to the machine or to its parts. It has been shown that frequencies may be determined by the method according to the invention that remain undetected during normal Fourier analysis.

The method according to the invention may be particularly advantageous in medical equipment e.g., for the evaluation of long-term EKG's, long-term blood-pressure measurements, etc. Regarding the evaluation of long-term EKG's for infarction patients, the method may be applied as follows: the sequence of beat-to-beat intervals of the long-term EKG which are the basis for most evaluation methods of long-term EKG's serves as the output signal. An attribute is then assigned to each measured value. Here, comparison to the previous measured value serves as the attribute, or more precisely, the quotient of the measured value itself and the previous measured value.

If, for example, a measured value is 3% shorter than the previous one, then this measured value is assigned the attribute "0.97." If it is 3% longer, then the quotient is 1.03. The criterion for the selection of a measured value might be a value between 1 and 1.05. Based on this criterion, all measured values would be selected as events that are larger, but not larger than 5% of the previous measured value. In an average long-term EKG, about 30% of all measured values correspond to this criterion.

The SBT corresponds to the average progression of measured values before, during, and after the event (here, increase in measured values in the output signal). The SBT may be quantified in different ways: for the estimation of future risk in patients after myocardial infarction, it has been useful to add the central value of the SBT to its subsequent value, and to subtract from this sum the sum of the two previous measured values. This so-called EDC-2 value may be viewed as a standard for the central increase, and allows a prediction regarding the survival chance of the patient. The greater this EDC-2 value is, then the greater the patient's chance of survival. The EDC-2 value quantifies the SBT, however, only in the immediate vicinity of the center, but parameters are conceivable that include long-term alterations to the SBT.

In the evaluation just described, an attribute was assigned the measured values of the original signal that creates the relationship to the immediately-preceding measured value, whereby the predominantly shorter frequencies of the output signal in the SBT are emphasized. Emphasis of longer frequencies may be achieved by assigning attributes to the measured values that compare the measured values over a longer period of time, which, for example, compares the sum of the values of a specific time period after the measured value with the sum of the values of a specific time period before the measured value.

It is further possible to assign the measured values of a time sequence (e.g., that of an EKG) with an attribute from a temporally-equal graphed time sequence (e.g., blood-pressure increase from a blood-pressure curve). If both time sequences are linked (in this example, via the baro-reflex: Blood-pressure increase causes pulse decrease; blood-pressure decrease causes pulse increase), the SBT filters clear oscillations out of the EKG signal. If this is not the case, there are no oscillations. The SBT is thus suited to proof or exclusion of coupling of different signals.

For a full understanding of the present invention, reference should now be made to the following detailed description of the preferred embodiments of the invention as illustrated in the accompanying drawings.

BRIEF DESCRIPTION OF THE DRAWINGS

FIG. 1 with the tables (a) through (f), is a schematic illustration of the evaluation of a sequence of discrete measured values according to the invention.

DESCRIPTION OF THE PREFERRED EMBODIMENTS

Figure 2:
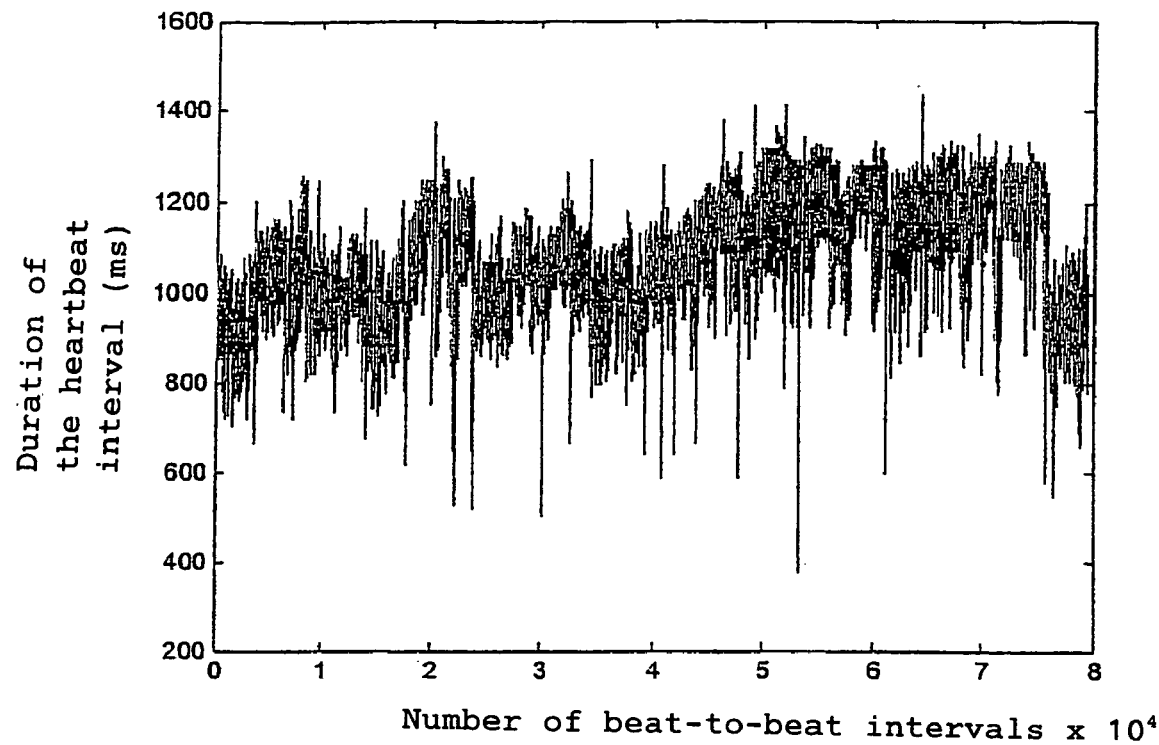
FIG. 2 is a so-called tachogram in which the time intervals between two sequential heartbeats over a period of 24 hours for a patient are recorded.

The preferred embodiments of the present invention will now be described with reference to FIGS. 1–13 of the drawings. Identical elements in the various figures are designated with the same reference numerals.

FIG. 1, with tables (a), (b), (c), (d), (e) and (f) demonstrates the overall principle of the present invention.

Table (a) lists the sequence of measured values to be analyzed.

According to Table (b), a freely-definable attribute is assigned to each measured value, i.e., the differential from the previous measured value.

In Table (c), a criterion that is applied to the attributes assigned to the measured values is defined. In this example, the criterion is fulfilled (K=1) when the attribute is positive (A>0). Measured values whose attributes fulfill the defined criterion are defined as events.

In Table (d), the events are entered into the table along with previous and subsequent measured values as an event chain so that measured values from the same position relative to the event are arranged vertically.

In Table (e), the Schmidt-Bauer Transformation is determined by averaging the event chains. This determines both the events themselves and the measured values of each same position relative to the event.

FIG. 2 is a tachogram, i.e., the sequence of time intervals between each pair of adjacent heartbeats (+RR intervals or RRI), in this case about 80,000 time intervals is entered opposite its number in the EKG. This tachogram is from a patient after myocardial infarction who survived for two more years.

Figure 3:
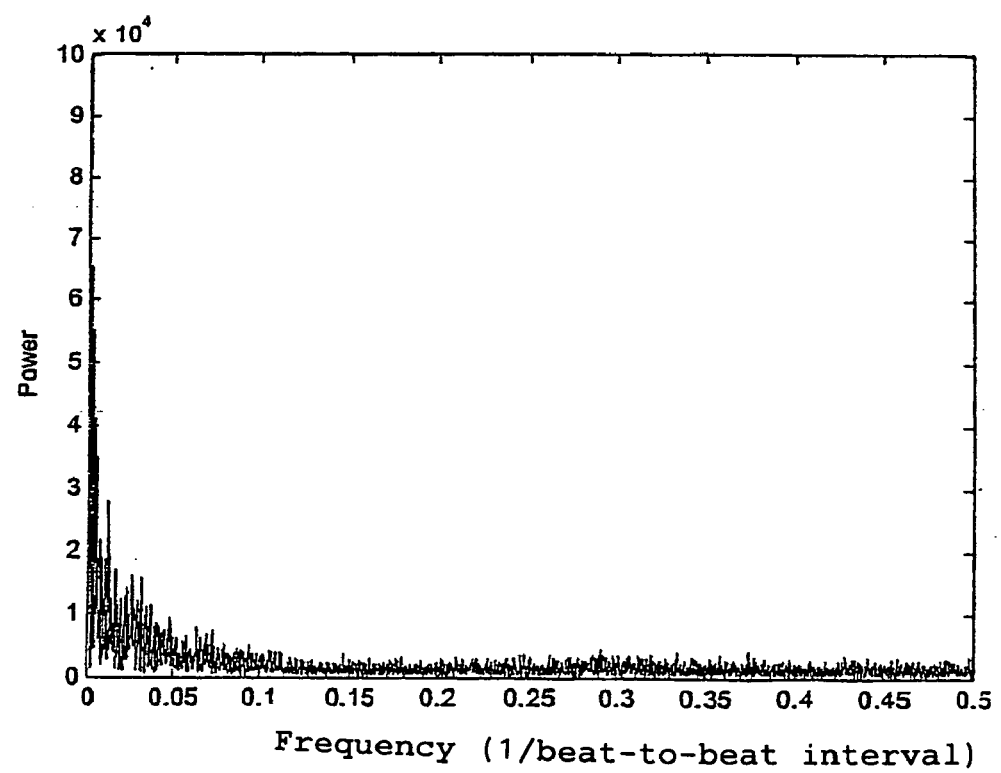
FIG. 3 is the frequency spectrum of the tachogram in FIG. 2 that was formed using a simple Fourier Transformation.

FIG. 3 shows the frequency spectrum of the tachogram shown in FIG. 2 that was determined by the use of simple Fourier Transformation as a function of the amplitude versus the frequency.

Figure 4:
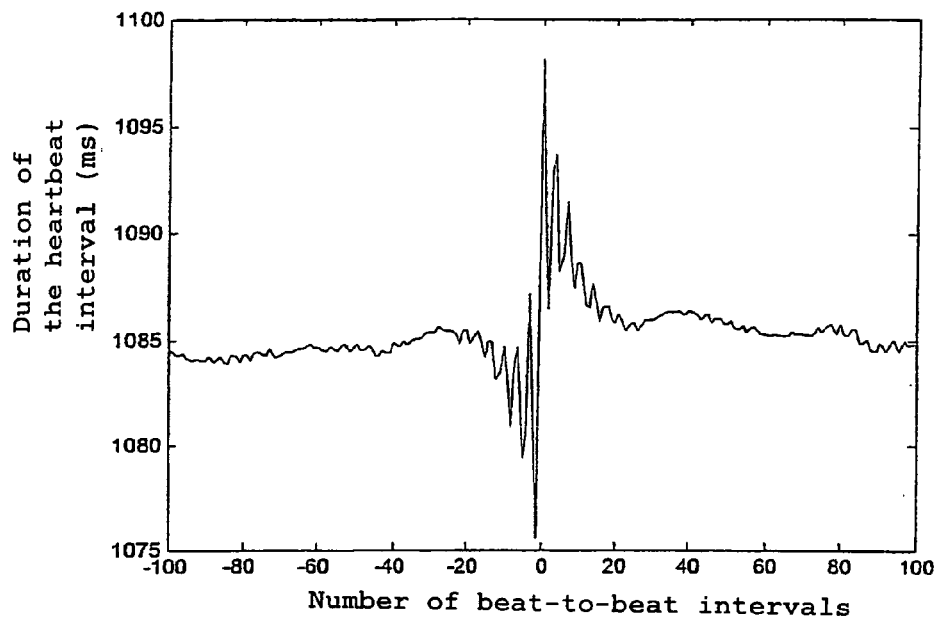
FIG. 4 is the Schmidt-Bauer Transformation of the tachogram in FIG. 2 according to the invention.

FIG. 4 shows the Schmidt-Bauer Transformation of the tachogram in FIG. 2 based on the invention. The quotient of the measured value itself and the previous measured value was selected as the attribute, and the criterion used was a value between 1 and 1.5. The chain length of the Schmidt-Bauer Transformation was established as 200 here, i.e., 100 values before and 100 values after the central event. The values of the transformation fluctuated about the value of 1,000 ms, whereby a significant dynamic may be established about the center at the zero value. Rapid modulations of beat-to-beat intervals may be limited by slower ones.

Figure 5:
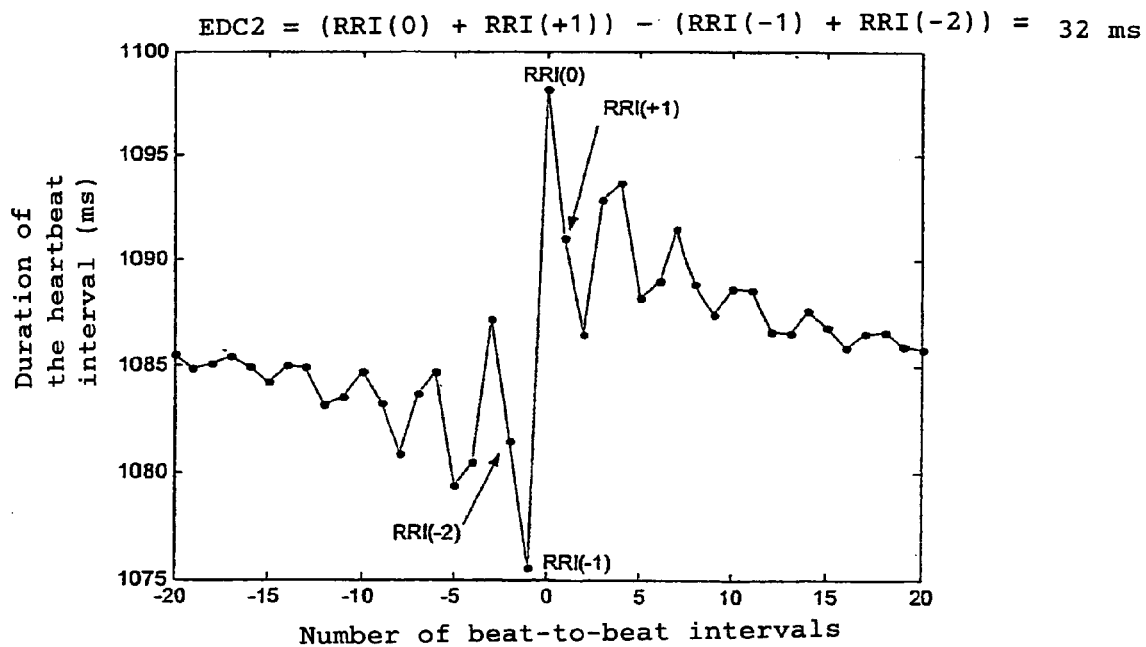
FIG. 5 is an extract from FIG. 4 that demonstrates the parameters EDC2.

FIG. 5 shows a section around the center of the Schmidt-Bauer Transformation according to FIG. 4, and demonstrates the calculation of the parameter EDC2 that is used to stratify risk. The values RRI(−2), RRI(−1), and RRI(+1) are entered along with the central event RRI(0). A characteristic value EDC2 may be calculated from:

$$EDC2=(RRI(0)+RRI(+1))-(RRI(-1)+RRI(-2))$$

A value of EDC2=32 ms results from the values of the curve shown.

Figure 6:
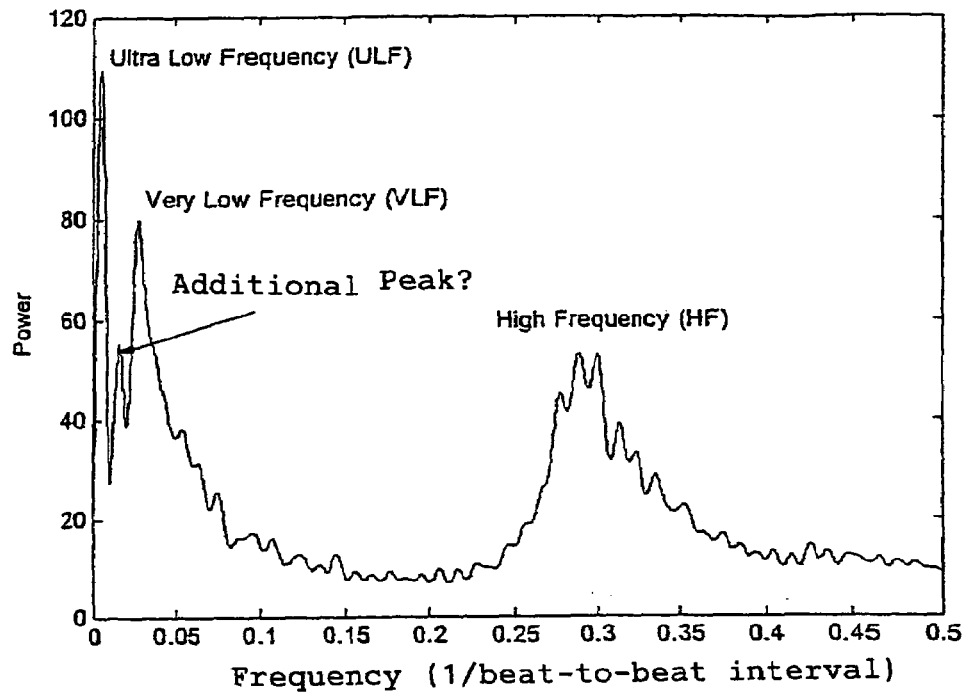
FIG. 6 is the frequency spectrum of the Schmidt-Bauer Transformation in FIG. 4.

FIG. 6 shows a simple Fourier Transformation of the Schmidt-Bauer Transformation as in FIG. 4. One may recognize clear peaks at about 0.003 Hz, 0.03 Hz, and 0.32 Hz that are not recognizable within the simple Fourier Transformation of the output signal. These three frequencies correspond in known ways to the physiological mechanisms of heart-frequency regulation. Thus, for example, the peak at 0.3 Hz corresponds to breath modulation of the heartbeat. Further, an additional peak is recognizable between 0.003 Hz and 0.03 Hz that was previously unrecognizable.

Figure 7:
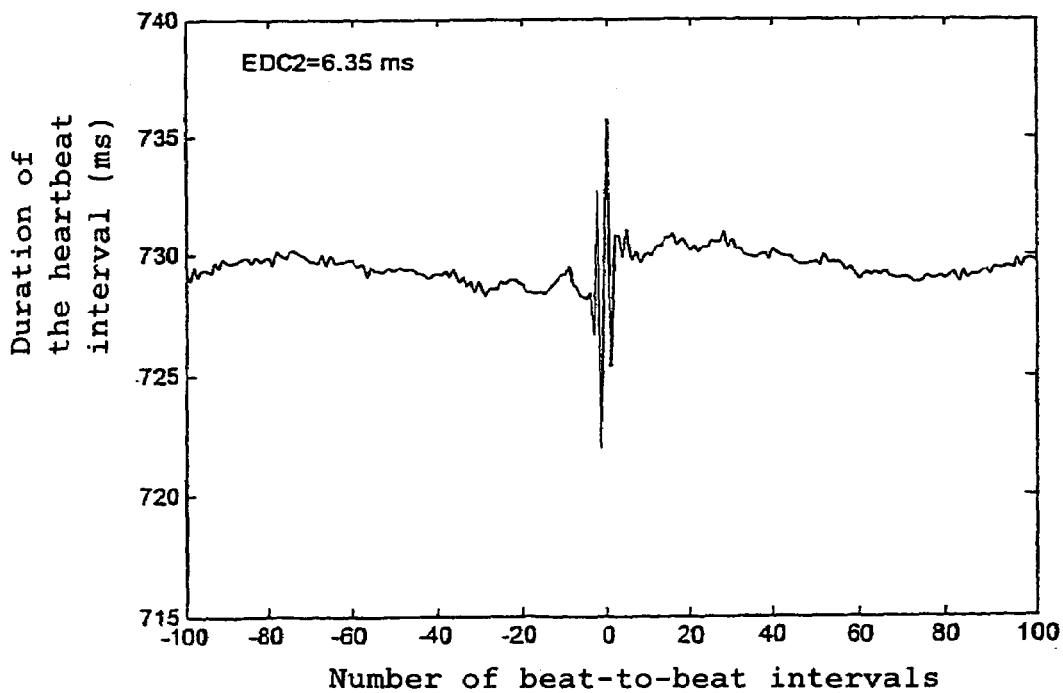
FIG. 7 is the Schmidt-Bauer Transformation from FIG. 4 of an at-risk myocardial infarction patient.

FIG. 7 shows a Schmidt-Bauer Transformation of a tachogram of a patient who died suddenly two years after myocardial infarction. One may recognize that the dynamic about the central event is clearly limited. The EDC2 value is clearly less at 6 ms.

Figure 8:
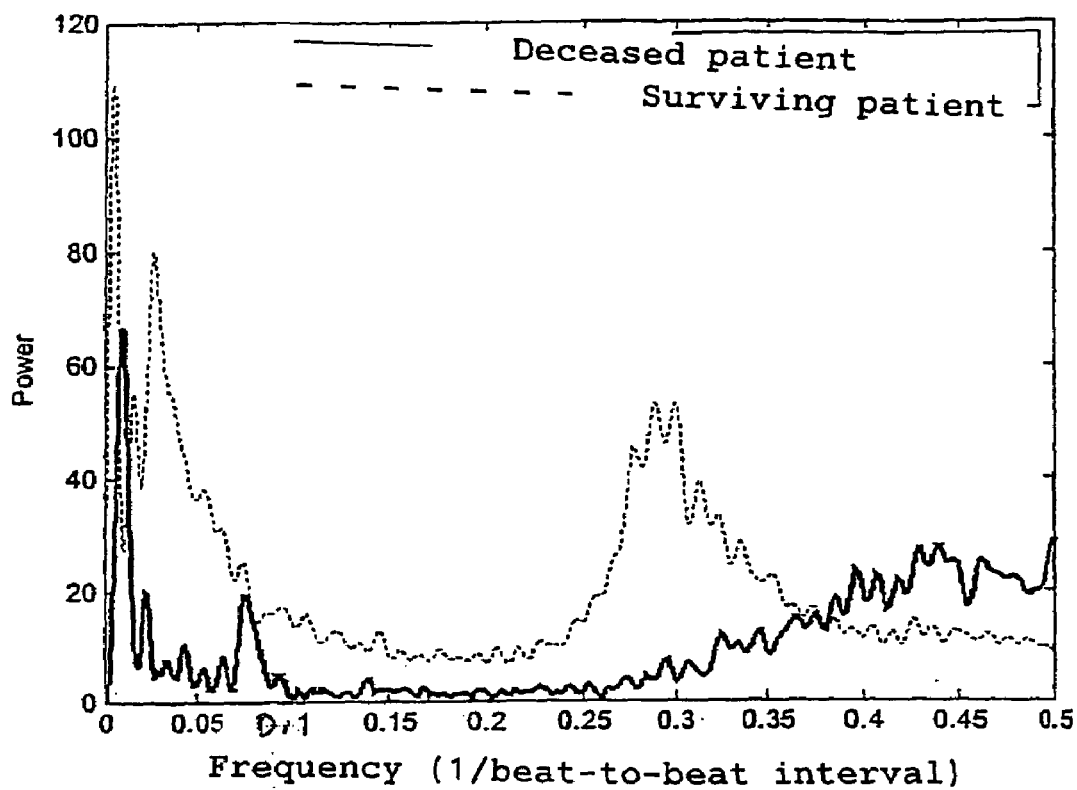
FIG. 8 is the frequency spectrum of the Schmidt-Bauer Transformation according to FIG. 7.

FIG. 8 shows the Fourier Transformation of the Schmidt-Bauer Transformation according to FIG. 7 (compare with the Fourier Transformation as in FIG. 6 shown as a dotted line). The peak in FIG. 6 recognizable at 0.3 Hz is not present, but instead a peak at about 0.75 Hz. This corresponds to the modulation of the heartbeat through the pressure receptors of the carotid artery, the so-called baroreceptors.

Figure 9:
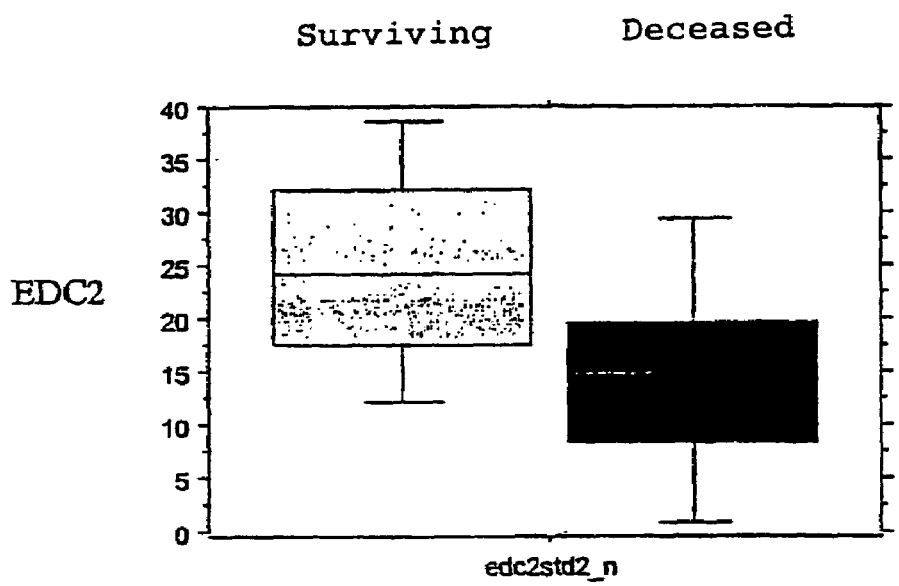
FIG. 9 is the distribution of EDC2 parameters for myocardial infarction patients who have survived for a longer period of time, and for myocardial infarction patients who died within a certain period of time.

FIG. 9 shows the differences in distribution of EDC2 values calculated for over 1,000 patients of the patients who survived an observation period of two years (Group 0), and for patients who died during that time period (Group 1). It is recognizable that the EDC2 values of the patients who die are clearly lower than the EDC2 values of the patients who survived this period. The significant predictive ability of EDC2 values has been tested and proved on over 4,000 myocardial infarction patients.

Figure 10:
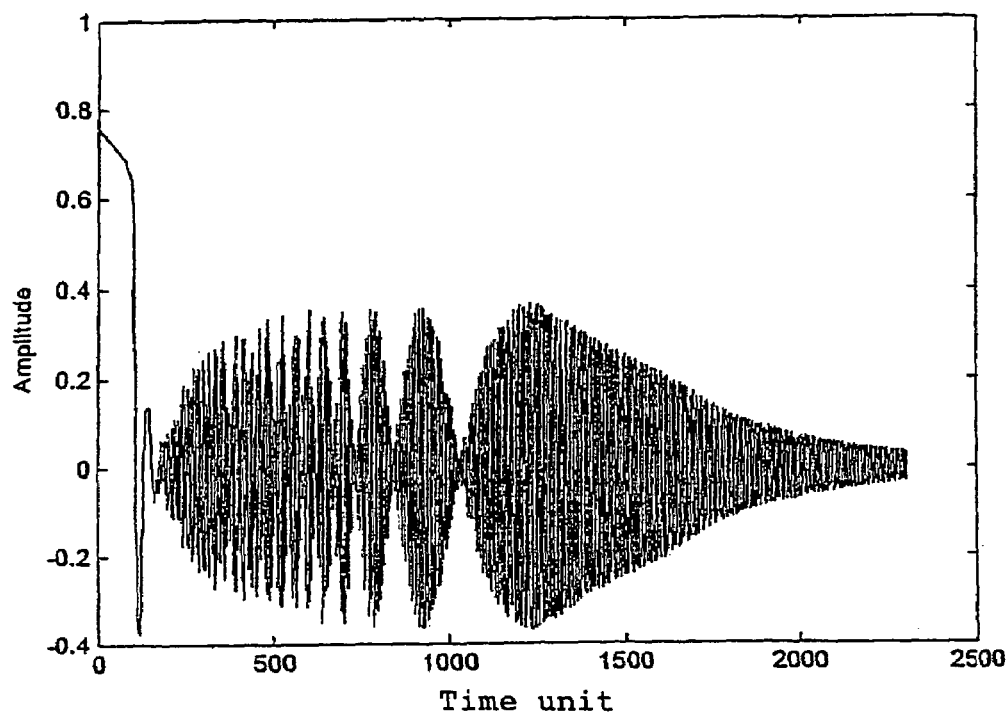
FIG. 10 is a representation of the amplitude of an oscillation versus time, in this case of the rotational acceleration of a truck wheel that is out of balance.

FIG. 10 shows the time behavior of the amplitude of an oscillation, in this case the oscillation in connection with the rotational acceleration of a truck wheel that is out of balance. This Figure shows amplitude versus time.

Figure 11:
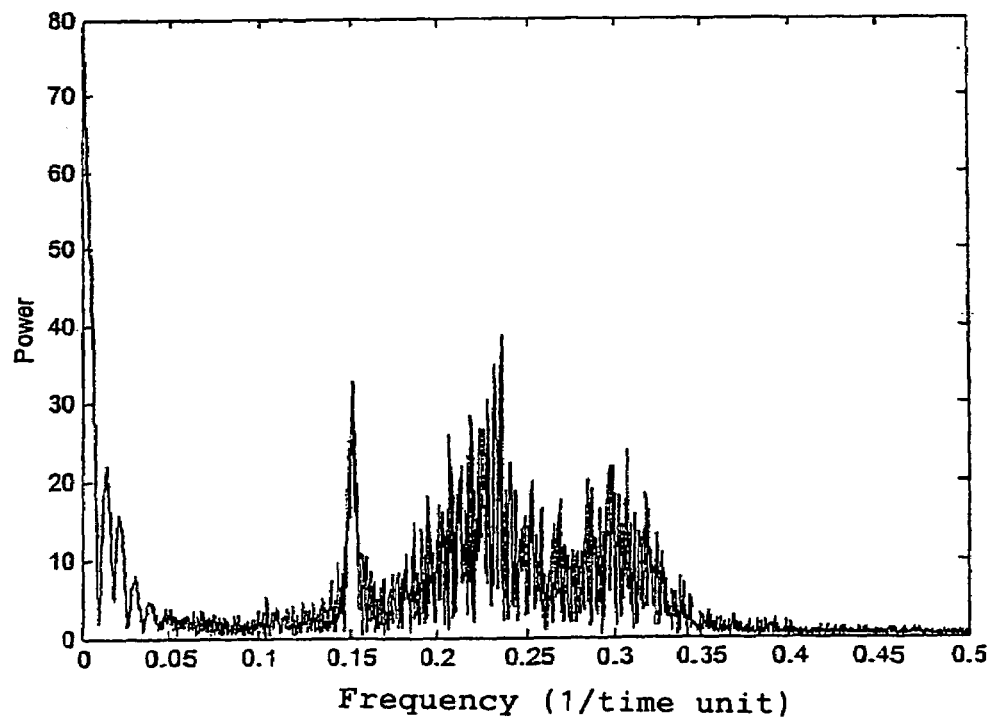
FIG. 11 is a simple Fourier Transformation of the oscillation according to FIG. 10.

FIG. 11 shows the Fourier Transformation of the original oscillation as in FIG. 8.

Figure 12:
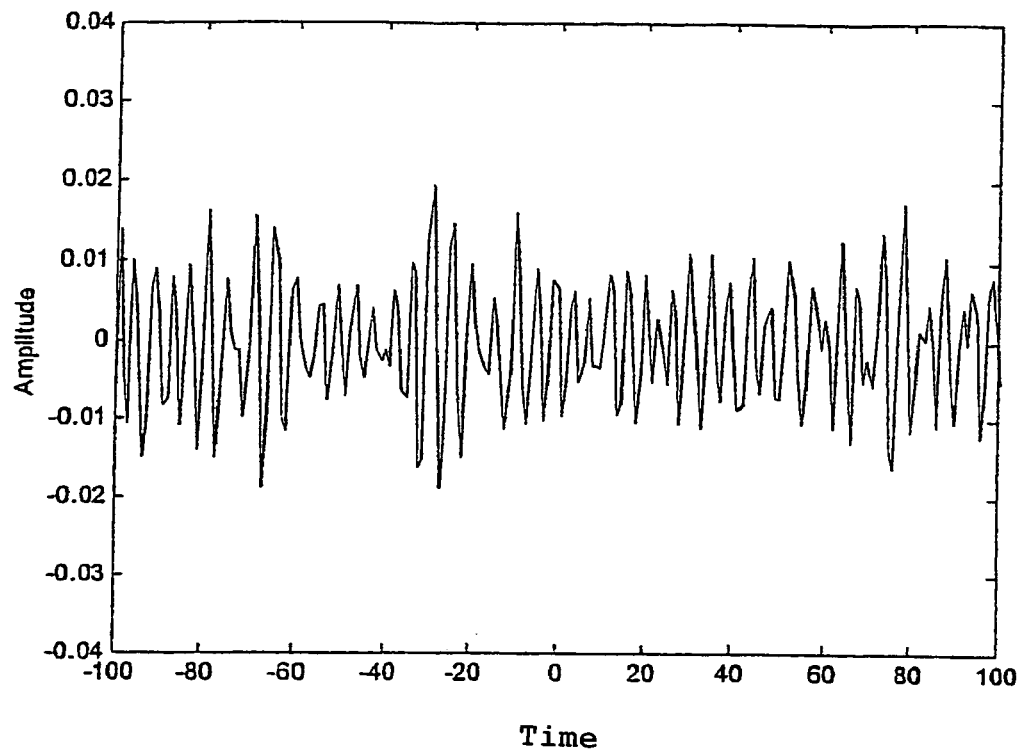
FIG. 12 is the Schmidt-Bauer Transformation of the oscillation according to FIG. 10 based on an evaluation using a method according to the invention.

FIG. 12 shows the Schmidt-Bauer Transformation of the oscillation according to FIG. 10. The difference from the previous measured value was used as the attribute, and a value greater than zero as the criterion.

Figure 13:
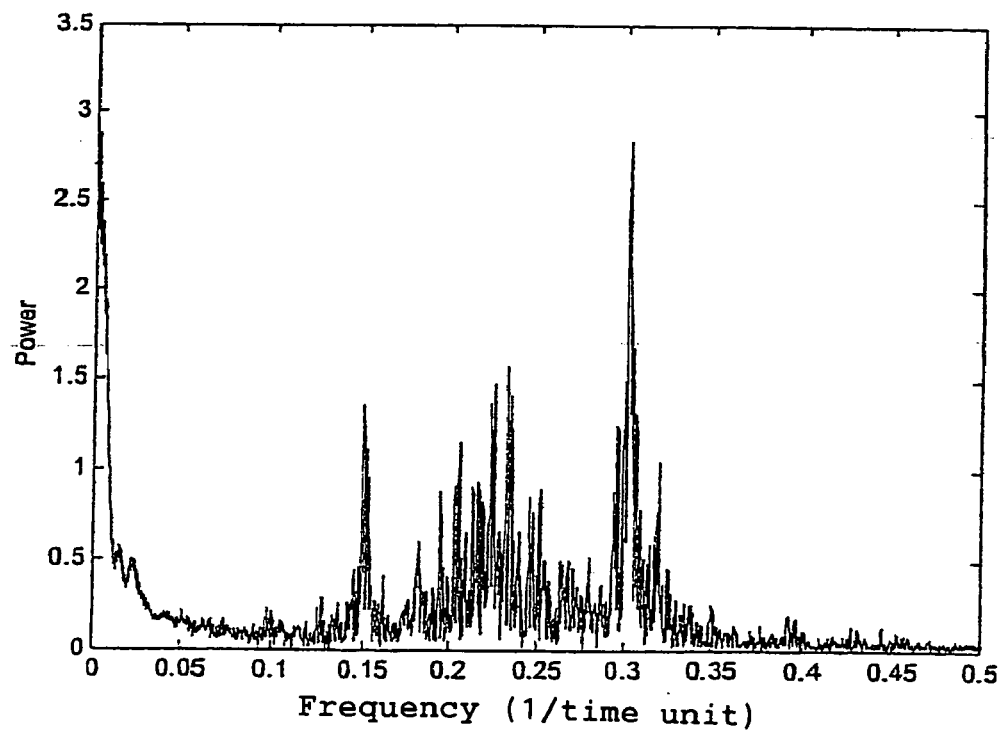
FIG. 13 is a Fourier Transformation of the Schmidt-Bauer Transformation shown in FIG. 12.

FIG. 13 shows the Fourier Transformation of the Schmidt-Bauer Transformation as in FIG. 10. One may see that this representation essentially agrees with the diagram in FIG. 11.

An important advantage is that the transformation represents a relatively short signal that, however, loses no information in comparison to a long output signal.

There has thus been shown and described a method for evaluating a sequence of discrete readings which fulfills all the objects and advantages sought therefor. Many changes, modifications, variations and other uses and applications of the subject invention will, however, become apparent to those skilled in the art after considering this specification and the accompanying drawings which disclose the preferred embodiments thereof. All such changes, modifications, variations and other uses and applications which do not depart from the spirit and scope of the invention are deemed to be covered by the invention, which is to be limited only by the claims which follow.

The invention claimed is:

1. A method for evaluating a sequence of discrete measured values, wherein an attribute is assigned to each measured value before evaluation, said attribute being derived from other measured values of the sequence of discrete measured values and including the same property for all measured values, and wherein a common criterion is established for the attributes thus assigned from the sequence of discrete measured values, said method comprising the following steps:

periodically sampling an analog signal and storing the sample as a sequence of discrete measured values;

designating as a specific event each of those measured values whose attribute fulfills the established common criterion;

selecting a chain of a specific length from the sequence of discrete measured values;

forming partial chains from the chain of specific length, each of which possesses a selected event as the center, whereby the other measured values of the partial chain are positioned in the original sequence on both sides of the central event;

positioning the measured values of the individual partial chains within the partial chain corresponding to their positions in that partial chain, such that the measured values of the central events are positioned together, and the measured values that are located at the same position about the central event are positioned together; and identifying and mathematically averaging all assigned measured values for the same position within the selected partial chains, and displaying the sequence of the thus-identified averaged measured values in the sequence determined by the chain of measured values.

2. Method as defined in claim 1, wherein the attribute is derived from the previous measured value.

3. Method as defined in claim 1, wherein the differential from the previous measured value is selected as the attribute for each measured value.

4. Method as defined in claim 3, wherein the criterion is designated as a measured value lies within a specific range with respect to the previous measured value.

5. Method as defined in claim 1, wherein defined measured value groups or functions of the measured values or measured value groups are selected in place of individual values.

6. Method as defined in claim 5, wherein the criterion is designated as one of a greater and smaller than the previous measured value.

7. Method as defined in claim 6, wherein the criterion is designated as being one of within a specific range larger and within a specific range smaller than the previous measured value.

8. Method as defined in claim 1, wherein the percent deviation is used as the criterion for adjacent measured values.

9. Method as defined in claim 1, wherein the evaluation of the sequence of discrete measured values is performed within the time or frequency domain.

10. Method as defined in claim 1, wherein the chain of measured values includes 200 or more measured values.

11. Method as defined in claim 1, wherein the quantity of selected chains is more than 4.

12. Method as defined in claim 11, wherein the quantity of selected chains is in the region of 10's.

13. Method as defined in claim 1, wherein each measured value represents a physiological value.

14. Method as defined in claim 13, wherein the physiological value is the time interval between two heartbeats.

15. Method as defined in claim 13, wherein the physiological value is blood pressure.

16. Method as defined in claim 1, wherein oscillation samples are evaluated using the method, whereby the oscillation sample is sampled with a high frequency, and the evaluated measured values are subjected to Fourier Transformation.

* * * * *